(12) United States Patent
Wu (10) Patent No.: US 8,809,809 B1
(45) Date of Patent: Aug. 19, 2014

(54) APPARATUS AND METHOD FOR FOCUSING IN FLUORESCENCE MICROSCOPE

(71) Applicant: Hong Kong Applied Science and Technology Research Institute Company Limited, Hong Kong (HK)

(72) Inventor: Xiaohua Wu, Hong Kong (HK)

(73) Assignee: Hong Kong Applied Science and Technology Research Institute Company Limited, Hong Kong Science Park, Shatin, New Territories, Hong Kong (CN)

( * ) Notice: Subject to any disclaimer, the term of this patent is extended or adjusted under 35 U.S.C. 154(b) by 0 days.

(21) Appl. No.: 14/038,770

(22) Filed: Sep. 27, 2013

(51) Int. Cl.
*G01N 21/64* (2006.01)
*G02B 21/16* (2006.01)

(52) U.S. Cl.
CPC ............... *G01N 21/64* (2013.01); *G02B 21/16* (2013.01)
USPC .................... 250/458.1; 250/459.1; 359/383; 348/79

(58) Field of Classification Search
USPC .................. 250/252.1, 458.1, 459.1; 348/79; 359/382, 383
See application file for complete search history.

(56) References Cited

U.S. PATENT DOCUMENTS

| 5,790,710 | A | 8/1998 | Price et al. |
| 6,154,282 | A | 11/2000 | Lilge et al. |
| 6,674,574 | B1 | 1/2004 | Aono |
| 7,141,773 | B2 | 11/2006 | Kaplan et al. |
| 2008/0204865 | A1* | 8/2008 | Yoneyama et al. ........... 359/381 |
| 2011/0298914 | A1* | 12/2011 | Oshiro et al. ................... 348/79 |

FOREIGN PATENT DOCUMENTS

WO         2007138369  A1     12/2007

* cited by examiner

*Primary Examiner* — Mark R Gaworecki
(74) *Attorney, Agent, or Firm* — Ella Cheong; Sam T. Yip (57) ABSTRACT

The presently claimed invention provides a focusing apparatus and method for a fluorescence microscope which is capable of shortening the time in focusing, increasing system throughput and avoiding from undesirable photo-bleaching. The fluorescence microscope of the present invention employs a portion of excitation light to form images of a sample to determine a focus plane for fluorescence imaging. As intensity of the portion of the excitation light is much higher than that of fluorescence light, the exposure time is highly reduced for image formation used for focusing purpose. The fluorescence microscope of the present invention enables to perform both predictive focusing and multiplex focusing.

20 Claims, 8 Drawing Sheets

APPARATUS AND METHOD FOR FOCUSING IN FLUORESCENCE MICROSCOPE

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to a fluorescence microscope, and particularly relates to a focusing apparatus and method for a fluorescence microscope.

BACKGROUND

A fluorescence microscope is an optical microscope that uses fluorescence and phosphorescence to generate an image. The specimen is illuminated with light of at least a specific wavelength, which is absorbed by the fluorophores, causing them to emit light of longer wavelengths. A typical fluorescence microscope includes a light source such as mercury arc lamp, an excitation filter, a dichroic beamsplitter, and an emission filter. The filters and the dichroic beamsplitter are chosen to match the spectral excitation and emission characteristics of the fluorophore used to label the specimen. Most fluorescence microscopes in use are epifluorescence microscopes, where excitation of the fluorophore and detection of the fluorescence are done through the same objective. These microscopes are widely used in biology and medical.

In order to acquire high-quality images in fluorescence microscopy systems, focusing is a crucial factor. Conventionally, microscopy focusing algorithms depend on the images themselves. A series of images at different focus planes is examined, and the image, having the largest amount of details, is selected as being correctly focused. For example, the focusing system takes a series of images around an estimated focus position. For each image, the system records its position, and computes a focus score which characterizes the sharpness of the respective image. Finally, the system computes a position for which the focus score is maximal, and the computed position is taken as the focus position.

U.S. Pat. No. 7,141,773 provides an imaging apparatus with an autofocus mechanism for obtaining focused images. The apparatus includes an objective lens, a focus controller for altering a distance between the objective lens and a sample, an object finder for finding objects of interest within the sample, and a light intensity measurement unit which measures light intensity levels of the thus identified objects of interest. The focus control alters the sample-objective distance to maximize the light intensity levels being measured, thereby to arrive at a focus position. Objects of interest may be identified by filtering out large objects and optionally by masking out background regions.

WO 2007138369 discloses a method and fluorescent imaging system for digitizing a specimen with fluorescent target points on a microscope slide. The method uses the fluorescence microscope system for detecting and scanning the fluorescent target points, and comprises the steps of marking the position of the specimen on the slide by visible marking means to define a specimen area containing the specimen and the fluorescent target points, capturing a bright field image of at least a portion of the slide at a first optical magnification, in which the portion contains the specimen area and determines a position of target fields falling within the specimen area from the visible marking means, and scanning the target fields of the specimen area at a second optical magnification higher than the first optical magnification, in which the scanning includes focusing on at least a part of the target fields.

The abovementioned prior arts are using the fluorescence-based focusing method, which enables focusing with high accuracy. Nevertheless, low fluorescence intensity requires long exposure to acquire an image with decent signal, so focus search based on multi-image comparison is slow. Furthermore, fluorescence intensity quickly decreases away from focus plane, thus making the focus search initiated far away from focus plane getting difficult. Long focusing time requires continuous excitation which may cause photobleaching. Slow focusing is particularly problematic for scanning a wide-field fluorescence microscopy. Ultimately, system throughput is getting low when too much time is taken for focusing.

For shortening the time for focusing and avoiding from photobleaching, non-fluorescence light is used for focusing. An additional light source such as halogen lamp is integrated with the fluorescence microscope for focusing. Mostly, other optical techniques such as phase contrast (PC) and differential interference contrast (DIC) are implemented as well in order to obtain high quality of focusing.

Phase contrast is an optical microscopy technique that converts phase shifts in light passing through a transparent specimen to brightness changes in the image. Phase shifts themselves are invisible, but become visible when shown as brightness variations. The basic principle to make phase changes visible in phase contrast microscopy is to separate the illuminating background light from the specimen scattered light, which makes up the foreground details, and to manipulate them differently. For performing such technique, special optics are employed like phase contrast annulus, condenser, and phase plate.

Differential interference contrast microscopy is also an optical microscopy illumination technique used to enhance the contrast in unstained, and transparent samples. DIC works on the principle of interferometry to gain information about the optical path length of the sample, to see otherwise invisible features. DIC works by separating a polarized light source into two orthogonally polarized mutually coherent parts which are spatially displaced (sheared) at the sample plane, and recombined before observation. Polarizer, DIC prism, condenser, analyzer are required for realizing the technique of DIC.

U.S. Pat. No. 5,790,710 teaches a phase-contrast autofocus for fluorescence microscopy.

U.S. Pat. No. 6,674,574 provides a focusing system for a microscope comprising an objective lens, a sample stage, a reflected illumination system for generating fluorescence from a sample, a transmitted illumination system for irradiating light on the sample to capture a transmitted optical image, a set of optical elements for forming the transmitted optical image on the basis of a phase information included in light transmitted through the sample, an optical element for dividing the fluorescence image and the transmitted optical image, a sensor for capturing the transmitted optical image divided by the optical element for dividing light, a focus detecting section for detecting a focusing level of the transmitted optical image on the basis of a signal output from the sensor, and a driver for moving at least one of the objective lens and the stage to focus on the sample on the basis of the focusing level.

Both U.S. Pat. No. 5,790,710 and U.S. Pat. No. 6,674,574 are using non-fluorescence based focusing method. They acquire an advantage in having fast speed in focusing. Nevertheless, their disadvantages are that only one focus is provided for all fluorescence channels, architecture of the microscope is complicate and much special optics are required.

Consequently, there is an unmet need for a focusing apparatus and method for fluorescence microscopy, especially wide-field scanning fluorescence microscopy applications like whole slide imaging and digital pathology, which provide fast speed in focusing under simple architecture and without employing too much special optics.

SUMMARY OF THE INVENTION

Accordingly, the presently claimed invention is to provide a focusing apparatus and method for a fluorescence microscope, which is able to reduce the time in focusing.

A first aspect of the present invention is to provide an apparatus for focusing in a fluorescence microscope.

In accordance with a first embodiment of the presently claimed invention, a focusing apparatus for a fluorescence microscope comprises: an excitation light source for emitting excitation light used to excite a sample; a beam splitter for reflecting the excitation light towards the sample via an objective lens, and transmitting fluorescence light emitted from the sample; and a focusing module located between the excitation light source and the beam splitter, wherein the focusing module comprises a reflecting optical device used for light reflection and a focus imaging camera, wherein the reflecting optical device is located in a pathway of the excitation light between the excitation light source and the beam splitter; wherein the sample reflects, backward scatters, or reflects and backward scatters a first portion of the excitation light towards the beam splitter, and the beam splitter reflects the first portion of the excitation light towards the reflecting optical device, and the reflecting optical device reflects a second portion of the excitation light towards the focus imaging camera; and wherein the second portion of the excitation light captured by the focus imaging camera forms at least one excitation light image of the sample for focusing of fluorescence imaging.

In accordance with a second embodiment of the presently claimed invention, a focusing apparatus for a fluorescence microscope comprises: an excitation light source for emitting excitation light used to excite a sample; a beam splitter for reflecting the excitation light towards the sample via a objective lens, and transmitting fluorescence light emitted from the sample; and a focusing module located beneath the sample, wherein the focusing module comprises a converging lens used for converging light, and a focus imaging camera, wherein the converging lens is located between the sample and the focus imaging camera; wherein a portion of the excitation light transmits through the sample, and the portion of the excitation light travels towards the converging lens, and is converged by the converging lens towards the focus imaging camera; and wherein the portion of the excitation light captured by the focus imaging camera forms at least one excitation light image of the sample for focusing of fluorescence imaging.

A second aspect of the present invention is to provide a method for focusing in a fluorescence microscope.

In accordance with an embodiment of the presently claimed invention, a focusing method for a fluorescence microscope comprises: emitting excitation light for illuminating a sample via an objective lens, wherein the excitation light is reflected towards the sample by a beam splitter; reflecting, backward scattering, or reflecting and backward scattering a first portion of the excitation light by the sample towards the beam splitter, reflecting the first portion of the excitation light by the beam splitter towards a reflecting optical device, and reflecting a second portion of the excitation light by the reflecting optical device towards a focus imaging camera; and forming at least one excitation light image with the second portion of the excitation light by the focus imaging camera for focusing of fluorescence imaging.

In accordance with another embodiment of the presently claimed invention, a focusing method for a fluorescence microscope comprises: emitting excitation light for illuminating a sample via an objective lens, wherein the excitation light is reflected towards the sample by a beam splitter; transmitting a portion of the excitation light through the sample, and converging the portion of the excitation light towards a focus imaging camera; and forming at least one excitation light image with the portion of the excitation light by the focus imaging camera for focusing of fluorescence imaging.

Due to using a portion of the excitation light for focusing, comparing with traditional fluorescence based focusing system, the portion of the excitation light carries much higher intensity in formation of detailed image for focusing, thereby enabling accurate focusing within short period, and avoiding from the undesirable photo-bleaching.

Unlike the traditional non-fluorescence based focusing system, the fluorescence microscope of the present invention requires only one light source. Furthermore, no special optics such as PC or DIC is required, and fluorescence light is free from any interference by the special optics and non-fluorescence light for focusing.

In addition, the focusing apparatus of the present invention is able to perform both multiplex focusing and predictive focusing simultaneously while both the fluorescence and non-fluorescence based focusing systems fail to do so.

BRIEF DESCRIPTION OF THE DRAWINGS

Embodiments of the present invention are described in more detail hereinafter with reference to the drawings, in which.

DETAILED DESCRIPTION OF PREFERRED EMBODIMENTS

In the following description, focusing apparatuses and methods for fluorescence microscopes are set forth as preferred examples. It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

Figure 1:
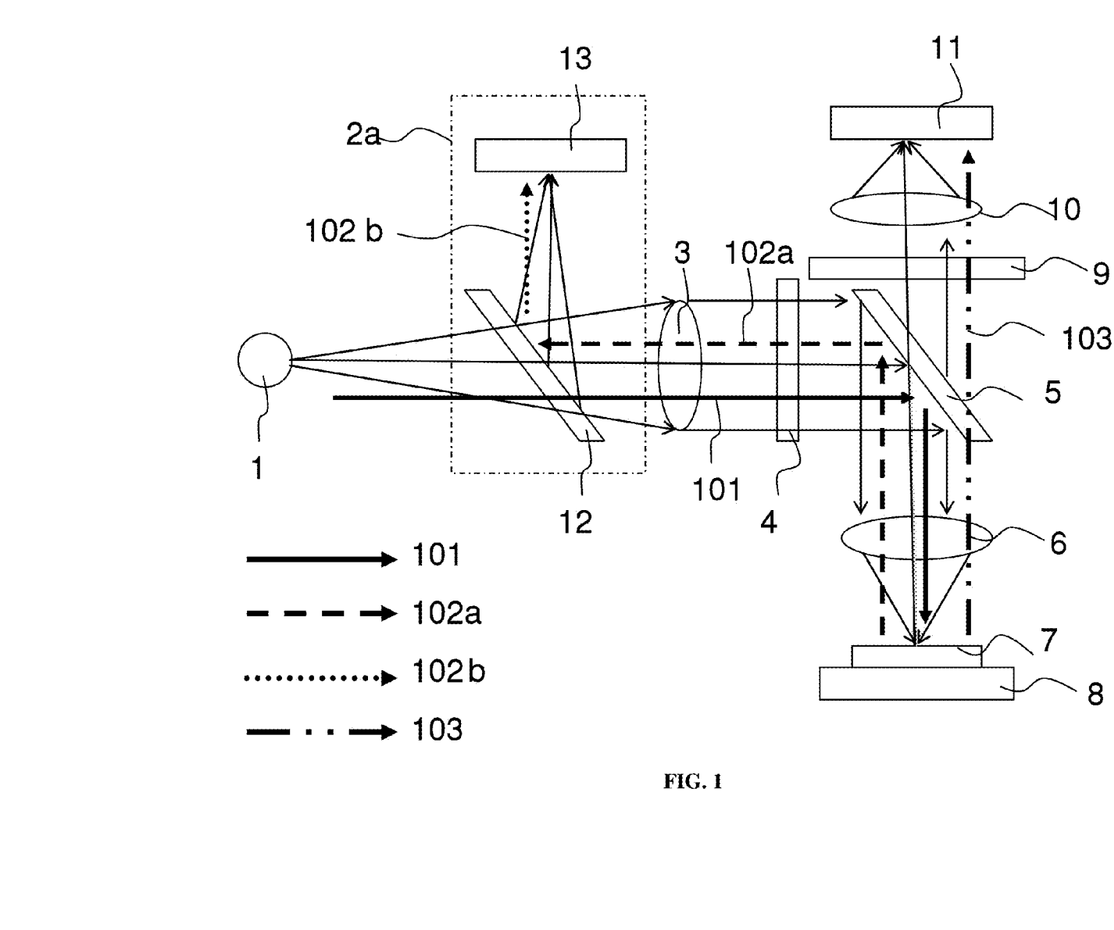
FIG. 1 shows a schematic diagram of a fluorescence microscope with a focusing apparatus using a portion of excitation light under reflecting and/or backward scattering mode according to a first embodiment of the presently claimed invention.

FIG. 1 shows a schematic diagram of a fluorescence microscope with a focusing apparatus using a portion of excitation light under reflecting and/or backward scattering mode according to a first embodiment of the presently claimed invention. The fluorescence microscope comprises an excitation light source 1, a focusing module 2a, a collector lens 3, an excitation filter 4, a dichroic beam splitter 5, an objective lens 6, a sample 7, a stage 8, an emission filter 9, a tube lens 10 and a fluorescence imaging camera 11. The focusing module 2a is located between the excitation light source 1 and the collector lens 3, and comprises a beam splitter 12 and a focus imaging camera 13. The beam splitter 12 is located in a pathway of the excitation light between the excitation light source 1 and the collector lens 3, and the focus imaging camera 13 is located on top of the beam splitter 12.

The excitation light source 1 can be a mercury arc lamp, xenon arc lamp, laser or light-emitting diode, which emits excitation light having specific wavelengths for irradiating the sample 7. The sample 7 contains fluorescence dye, and emits fluorescence light when it is irradiated. The focusing module 2a is used to determine focus planes of the sample 7 for fluorescence imaging. The focus plane is a plane where the sample surface positions form an in-focus image at the fluorescence imaging camera. The collector lens 3 is used to converge the excitation light from the excitation light source 1. The excitation filter 4 is used to select the excitation light with a specific band of wavelengths to pass through. The dichroic beam splitter 5 is used to reflect the excitation light and transmit the fluorescence light emitted from the sample 7. The stage 8 is used to hold the sample 7. The objective lens 6 is used to focus the excitation light onto the sample 7 and collect both the emitted fluorescence light and reflected/backward scattered excitation light. The emission filter 9 is used to filter out any noise signal of light, which can affect fluorescence imaging. The tube lens 10 is used to converge the fluorescence light onto the fluorescence imaging camera 11. The fluorescence imaging camera 11 is used to form fluorescence images and includes light sensors for capturing the fluorescence light from the sample 7. Preferably, the fluorescence imaging camera 11 is a charged couple device (CCD) camera. The beam splitter 12 can split a light beam into two, including a transmitted one and a reflected one. The amount of light being transmitted and reflected can be adjusted by using different beam splitters. The focus imaging camera 13 is used to form excitation light images of the sample for focusing of fluorescence imaging, and includes light sensors for capturing any portion of the excitation light under reflecting and/or backward scattering by the sample 7. The excitation light image is formed from the portion of the excitation light.

The excitation light passes through the beam splitter 12, the collector lens 3, and the excitation filter 4, and then arrives at the dichroic beam splitter 5. The excitation light is then reflected by the dichroic beam splitter 5, passes through the objective lens 6, and finally is converged on the sample 7. An arrow 101 shows the pathway of the excitation light.

After the irradiation of the sample 7 by the excitation light, a first portion of the excitation light is reflected and/or backward scattered by the sample 7, and collected by the objective lens 6 and the dichroic beam splitter 5. The dichroic beam splitter 5 reflects the first portion of the excitation light towards the excitation filter 4, the collector lens 3, and then the beam splitter 12. The beam splitter 12 reflects a second portion of the excitation light towards the focus imaging camera 13 to form excitation light images for focusing of fluorescence imaging. Hence the second portion of the excitation light is a portion of the first portion of the excitation light. Arrows 102a and 102b show the pathways of the first and the second portion of the excitation light respectively.

According to various embodiments of the presently claimed invention, the beam splitter 12 can be replaced by any reflecting optical device, which is able to totally or partially reflect the first portion of the excitation light towards the focus imaging camera 13 meanwhile minimizing its reduction of the excitation light intensity from the excitation light source 1 during transmission.

According to another embodiment of the presently claimed invention, the beam splitter 12 can be replaced by a mirror, which is able to totally reflect the first portion of the excitation light towards the focus imaging camera 13. Thus, the second portion of the excitation light is same as the first portion of the excitation light. Preferably, the mirror is smaller than a cross section of the pathway of the excitation light where the mirror is located at so that the transmission of the excitation light is not greatly affected.

Under the irradiation of the excitation light, the sample 7 emits fluorescence light having longer wavelengths comparing to the excitation light. The fluorescence light passes through the objective lens 6, the dichroic beam splitter 5, the emission filter 9, the tube lens 10, and finally arrives at the fluorescence imaging camera 11 for formation of fluorescence images. An arrow 103 shows the pathway of the fluorescence light.

The focus imaging camera 13 is employed to form excitation light images of the sample 7 with the second portion of the excitation light. As the intensity of the second portion of the excitation light is much higher than that of the fluorescence light, even with several orders of magnitude in some cases, an excitation light image of the sample can be formed within short period since the time for storing enough amount of light for imaging is highly reduced. Then, the formed excitation light images are further used for finding out a focus plane of the sample for the fluorescence imaging.

Comparing with the traditional method using fluorescence light for focusing, the present invention is capable of shortening the time for focusing, ultimately increasing system throughput and avoiding undesirable fluorescence photobleaching. In addition, comparing with the non-fluorescence based focusing method, the architecture of the fluorescence microscope of the present invention is much simpler because only one light source is needed, and there is no special optics for the PC or DIC. Additionally, as no special optics is required in the present invention, the fluorescence light can be avoided from interference by the special optics in light paths. And because of the simple system architecture, complicated synchronization signaling and mechanical movement in PC/DIC and fluorescence combination microscopes for focusing and imaging are avoided.

Figure 2:
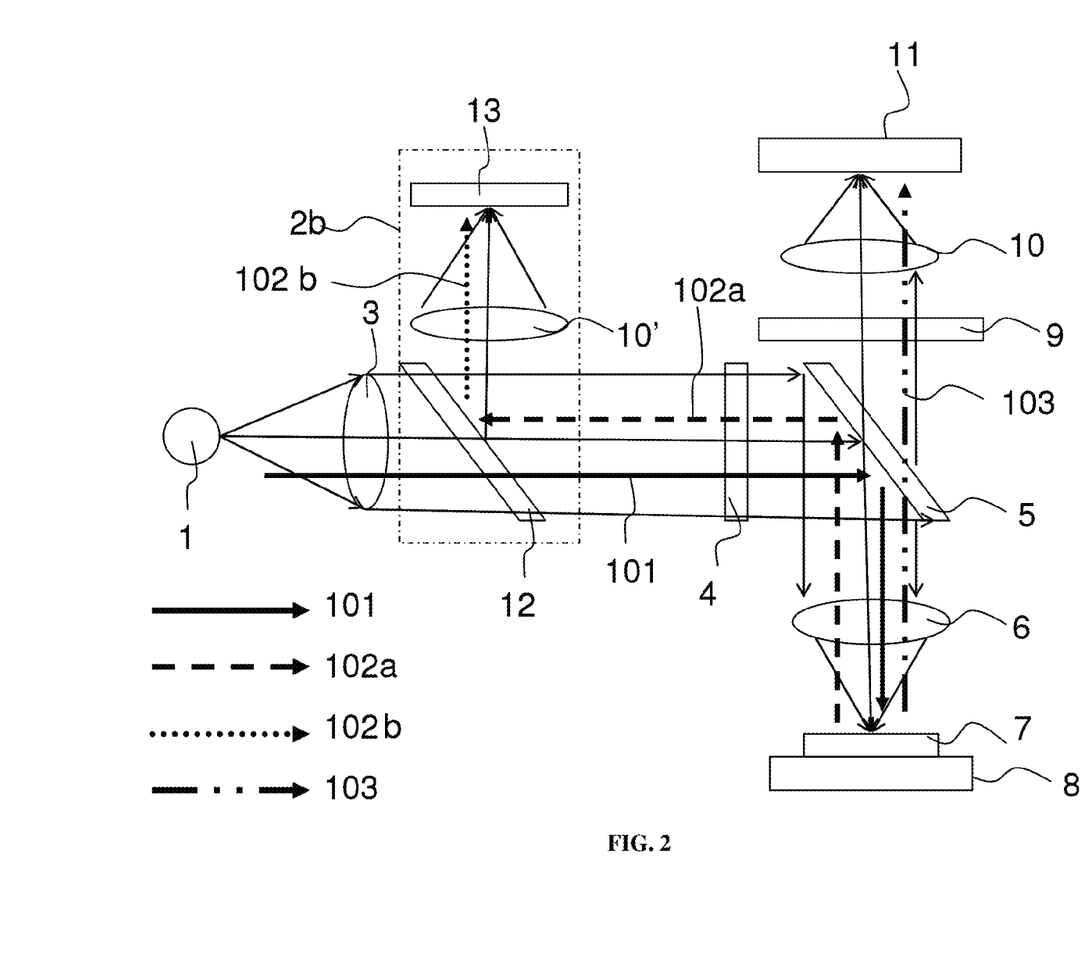
FIG. 2 shows a schematic diagram of a fluorescence microscope with a focusing apparatus using a portion of excitation light under reflecting and/or backward scattering mode according to a second embodiment of the presently claimed invention.

FIG. 2 shows a schematic diagram of a fluorescence microscope with a focusing apparatus using a portion of excitation light under reflecting and/or backward scattering mode according to a second embodiment of the presently claimed invention. The fluorescence microscope comprises the excitation light source 1, a focusing module 2b, the collector lens 3, the excitation filter 4, the dichroic beam splitter 5, the objective lens 6, the sample 7, the stage 8, the emission filter 9, the tube lens 10 and the fluorescence imaging camera 11. The focusing module 2b is located between the collector lens 3 and the excitation filter 4, and comprises the beam splitter 12, a tube lens 10', and the focus imaging camera 13. The beam splitter 12 is located in a pathway of the excitation light between the collector lens 3 and the excitation filter 4, and the tube lens 10' is located between the beam splitter 12, and the focus imaging camera 13.

The tube lens 10' is used for converging the second portion of the excitation light onto the focus imaging camera 13. Comparing with the first embodiment, although an extra tube lens is required, this configuration enhances the flexibility of optical design since the excitation light image formation by the focus imaging camera 13 is no longer dictated by the collector lens 3, taking a major function in focusing the excitation light towards the excitation filter 4 and the dichroic beam splitter 5. Hence higher freedom in optical designs of the focusing module 2b is provided such as the size and covered sample area of the focusing module 2b in this embodiment.

According to various embodiments of the presently claimed invention, the beam splitter 12 can be replaced by any reflecting optical device, which is able to totally or partially reflect the first portion of the excitation light towards the focus imaging camera 13 meanwhile minimizing its reduction of the excitation light intensity from the excitation light source 1 during transmission.

According to another embodiment of the presently claimed invention, the beam splitter 12 can be replaced by a mirror, which is able to totally reflect the first portion of the excitation light towards the focus imaging camera 13. Thus, the second portion of the excitation light is same as the first portion of the excitation light. Preferably, the mirror is smaller than a cross section of the pathway of the excitation light where the mirror is located at so that the transmission of the excitation light is not greatly affected.

Figure 3:
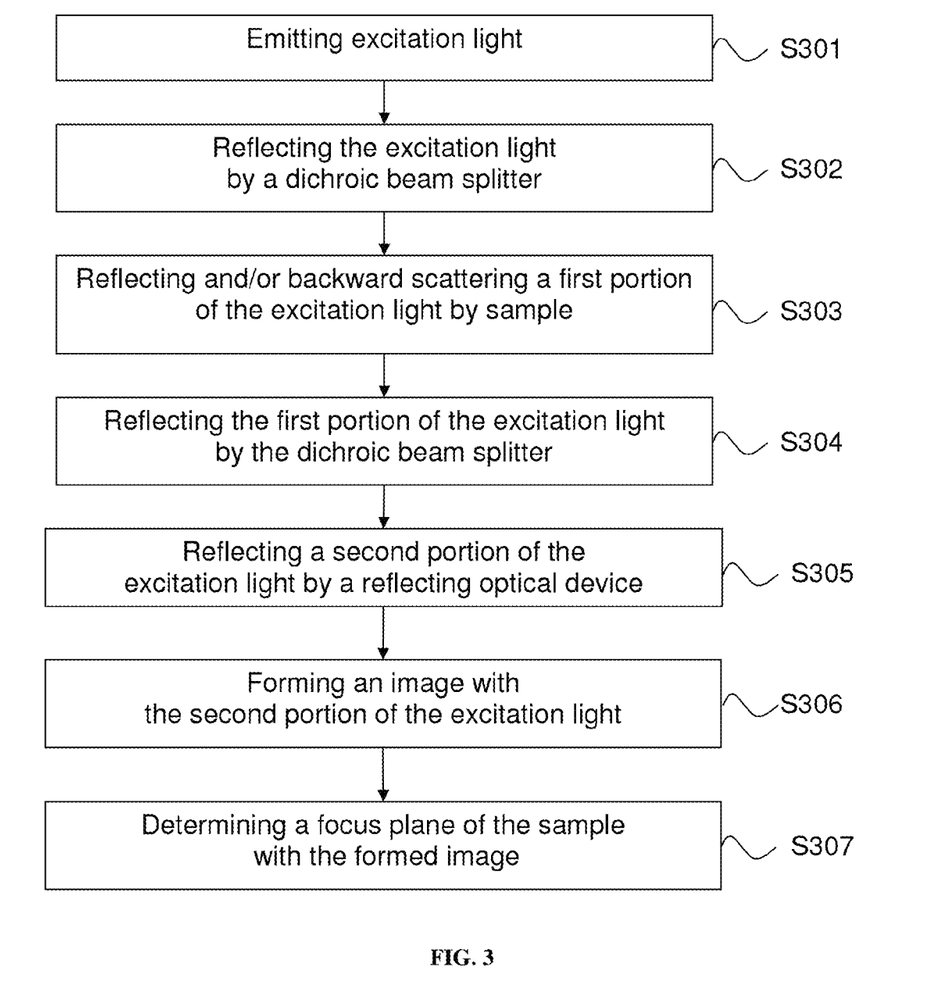
FIG. 3 is a flowchart illustrating steps of a focusing method for a fluorescence microscope using a portion of excitation light under reflecting and/or backward scattering mode according to an embodiment of the presently claimed invention.

FIG. 3 is a flowchart illustrating steps of a focusing method for a fluorescence microscope using a portion of excitation light under reflecting and/or backward scattering mode according to an embodiment of the presently claimed invention. In step 301, excitation light is emitted from an excitation light source towards a dichroic beam splitter through a focusing module and a collector lens. The focusing module comprises a reflecting optical device and a focus imaging camera, and the reflecting optical device is located in a pathway of the excitation light between the excitation light source and the dichroic beam splitter. In step 302, the excitation light is reflected by the dichroic beam splitter towards a sample dyed with fluorescent material through an objective lens. In step 303, a first portion of the excitation light is reflected and/or backward scattered by the sample towards the dichroic beam splitter through the objective lens. In step 304, the first portion of the excitation light is reflected by the dichroic beam splitter towards the reflecting optical device. In step 305, a second portion of the excitation light is reflected by the reflecting optical device towards the focus imaging camera. The second portion of the excitation light is a portion of the first portion of the excitation light, or same as the first portion of the excitation light. In step 306, an excitation light image of the sample is formed with the second portion of the excitation light by the focus imaging camera. In step 307, a focus plane of the sample for fluorescence imaging is determined based on the formed excitation light image.

Figure 4:
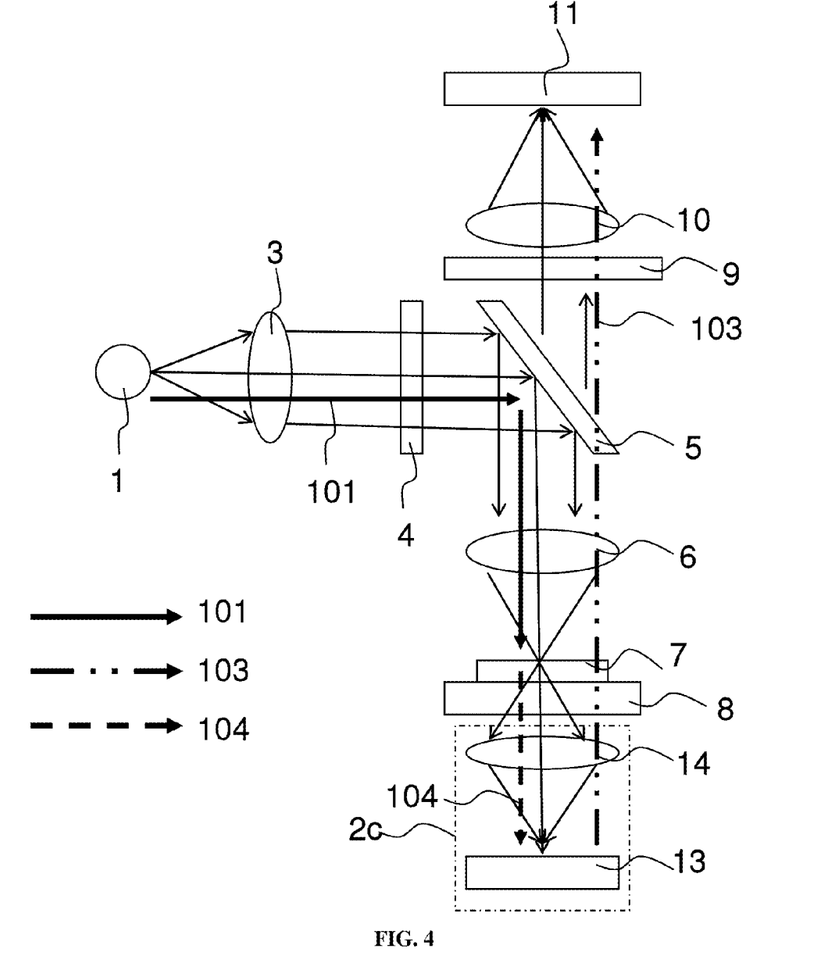
FIG. 4 shows a schematic diagram of a fluorescence microscope with a focusing apparatus using a portion of excitation light under transmitting mode according to an embodiment of the presently claimed invention.

FIG. 4 shows a schematic diagram of a fluorescence microscope with a focusing apparatus using a portion of excitation light under transmitting mode according to an embodiment of the presently claimed invention. The fluorescence microscope comprises the excitation light source 1, a focusing module 2c, the collector lens 3, the excitation filter 4, the dichroic beam splitter 5, the objective lens 6, the sample 7, the stage 8, the emission filter 9, the tube lens 10 and the fluorescence imaging camera 11. The focusing module 2c is located beneath the stage 8, and comprises a converging lens 14, and the focus imaging camera 13. The converging lens 14, located between the stage 8 and the focus imaging camera 13, and in a pathway of the portion of the excitation light, is used for converging the portion of the excitation light onto the focus imaging camera 13.

During the irradiation of the sample 7 by the excitation light from the excitation light source 1, a portion of the excitation light transmits through the sample 7. The portion of the excitation light passes through the stage 8, containing a through hole for light transmission, and arrives at the converging lens 14, and then is focused on the focus imaging camera 13 by the converging lens 14. Preferably, the converging lens 14 is a long-working distance objective lens, a low magnification objective lens, or a lens group to form high resolution images. An arrow 104 shows the pathway of the portion of the excitation light.

Similarly, the portion of the excitation light under the transmitting mode is used to form excitation light images of the sample 7 with the focus imaging camera 13. As the intensity of the portion of the excitation light is much higher than that of the fluorescence light, an exposure time for focusing is highly shortened.

Figure 5:
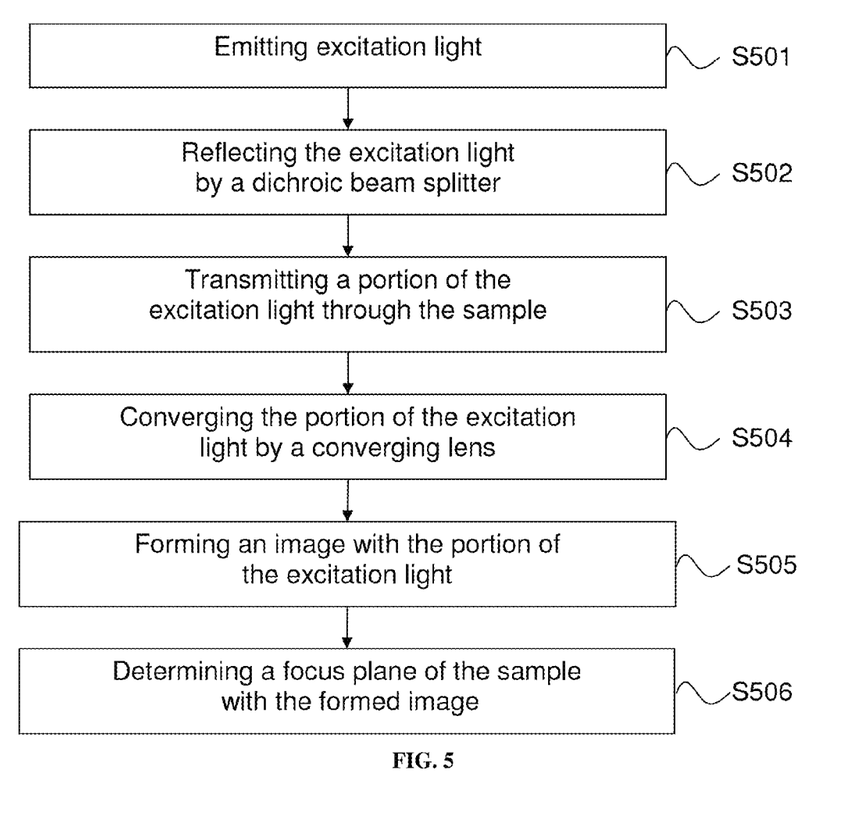
FIG. 5 is a flowchart illustrating steps of a focusing method for a fluorescence microscope using a portion of excitation light under transmitting mode according to an embodiment of the presently claimed invention.

FIG. 5 is a flowchart illustrating steps of a focusing method for a fluorescence microscope using a portion of excitation light under transmitting mode according to an embodiment of the presently claimed invention. In step 501, excitation light is emitted from an excitation light source towards a dichroic beam splitter through a collector lens. In step 502, the excitation light is reflected by the dichroic beam splitter towards a sample dyed with fluorescent material through an objective lens. In step 503, a portion of the excitation light is transmitted through the sample towards a focusing module. The focusing module comprises a converging lens and a focus imaging camera, and the converging lens is located between the sample and the focus imaging camera. In step 504, the portion of the excitation light is converged by the converging lens towards the focus imaging camera. In step 505, an excitation light image of the sample is formed with the potion of the excitation light by the focus imaging camera. In step 506, a focus plane of the sample is determined for fluorescence imaging based on the formed excitation light image.

According to one embodiment of the present invention, the fluorescence microscope further comprises a central processing unit, CPU, in order to determine the focus plane of a sample. The CPU, connected with the focus imaging camera, stage, and fluorescence imaging camera, is used for analyzing excitation light images taken by the focus imaging camera, determining whether a fluorescence image is in focus plane or not, adjusting lens-to-sample distance through movement of the stage, and instructing the fluorescence imaging camera to take fluorescence images once the sample is in focus.

Figure 6:
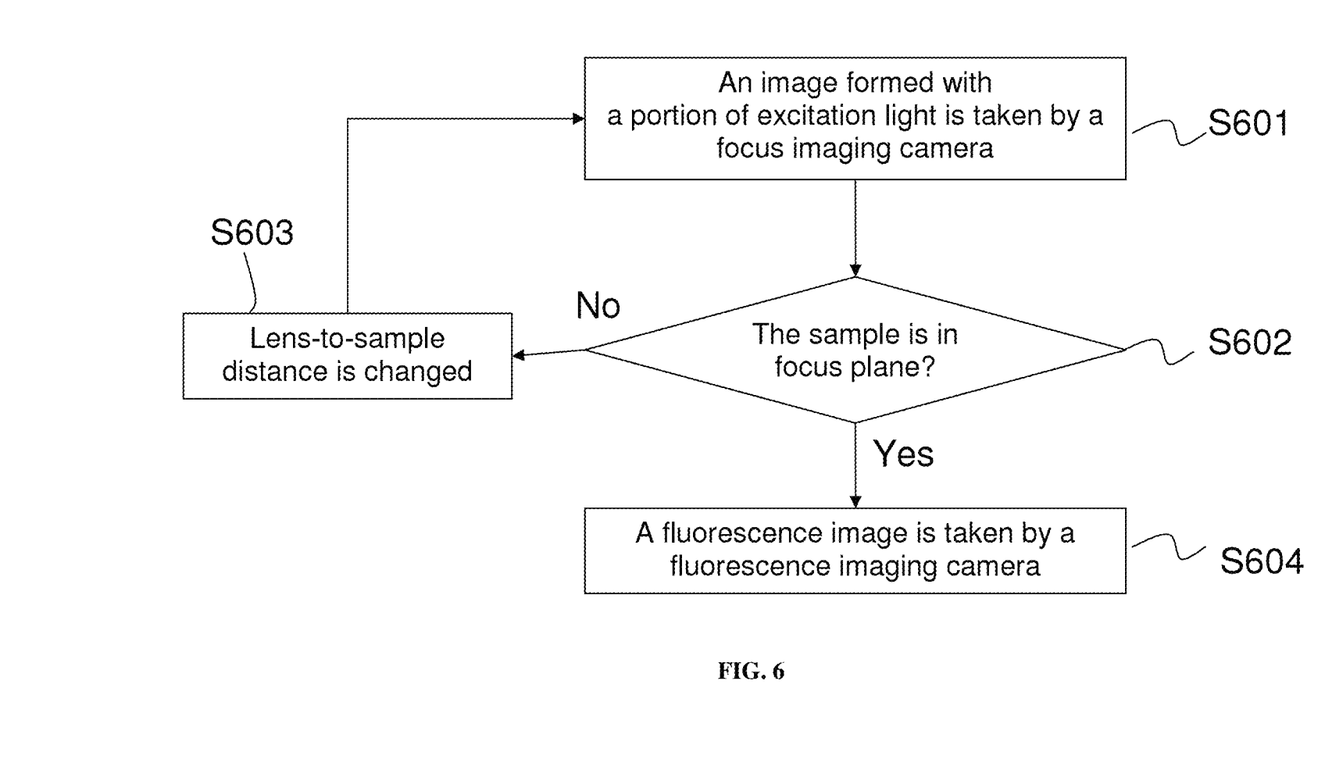
FIG. 6 is a flowchart illustrating steps of a focusing method by changing lens-to-sample distance according to an embodiment of the presently claimed invention.

FIG. 6 is a flowchart illustrating steps of a focusing method by changing lens-to-sample distance according to an embodiment of the presently claimed invention. In step 601, an excitation light image of a sample formed from a portion of excitation light is taken by a focus imaging camera. In step 602, the excitation light image is checked whether the sample is in focus plane for fluorescence imaging. If not, lens-to-sample distance is changed in step 603, and the steps from 601 to 602 are repeated. If yes, a fluorescence image is taken by a fluorescence imaging camera in step 604. Preferably, the lens-to-sample distance is changed through linear movement of the stage controlled by a motor.

Since a field of view of the focus imaging camera can be different from a field of view of fluorescence imaging camera, the fluorescence microscope of the present invention enables to perform predictive focusing, which is a focusing method that during taking a fluorescence image at a field of view, focusing at a next field of view can be performed as well. The predictive focusing is capable of further reducing the time in fluorescence imaging since taking fluorescence image and focusing take place in parallel.

Figure 7:
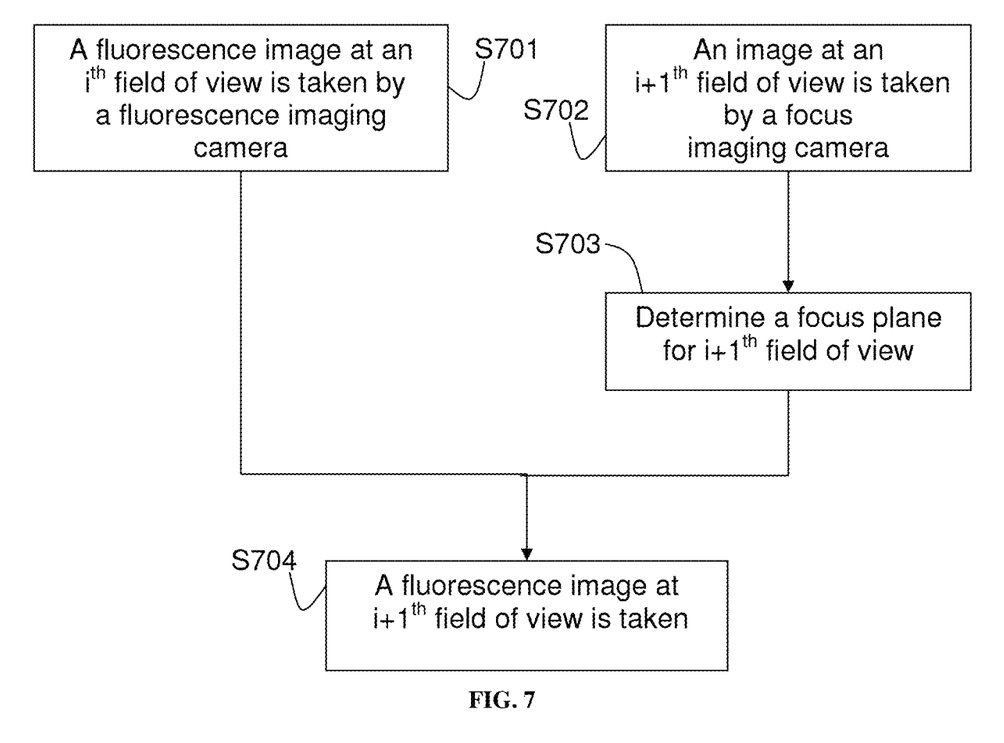
FIG. 7 is a flowchart illustrating steps of a predictive focusing method for a scanning fluorescence microscope according to an embodiment of the presently claimed invention.

FIG. 7 is a flowchart illustrating steps of a predictive focusing method for a scanning fluorescence microscope according to an embodiment of the presently claimed invention. In step 701, a sample is irradiated by excitation light, and a fluorescence image is taken at an $i^{th}$ field of view of the sample by a fluorescence imaging camera with fluorescence light from the sample. In step 702, an excitation light image is taken at an $i+1^{th}$ field of view by a focus imaging camera with a portion of the excitation light. In step 703, a focus plane for the $i+1^{th}$ field of view is determined based on the excitation light image. In step 704, a fluorescence image is taken at the $i+1^{th}$ field of view with the focus plane determined in step 703.

Accordingly, the traditional fluorescence-based focusing fails to perform the predictive focusing because only one imaging camera is used for both fluorescence imaging and focus imaging, thus, the two tasks cannot be handled simultaneously by the single camera. On the other hand, although the non-fluorescence based focusing is able to perform predictive focusing, the fluorescence imaging quality is frequently deteriorated since there are two beams of lights come from two different light sources in the same light pathway, thereby leading to interference between the two light beams. In contrast, the predictive focusing of the present invention is avoided from the abovementioned problems since there is only one light source used.

The present invention enables to perform multiplex focusing, which is used to find focus planes of a sample under different fluorescence excitation and emission channels. According to one embodiment of the present invention, more than one excitation filter, dichroic beam splitter, and emission filter are used to form various filter combination optical blocks. The filter combination optical blocks can be further configured to form a filter block turret, which can be rotated in the fluorescence microscope to change excitation light with different bands of wavelengths for sample irradiation. Accordingly, the non-fluorescence based focusing method such as PC or DIC fails to perform multiplex focusing since only one light source for focusing is unable to adapt to frequently-changed excitation lights of different bands of wavelengths. In contrast, the present invention enables to change the light for focusing simultaneously with the change of excitation light for fluorescence.

Figure 8A:
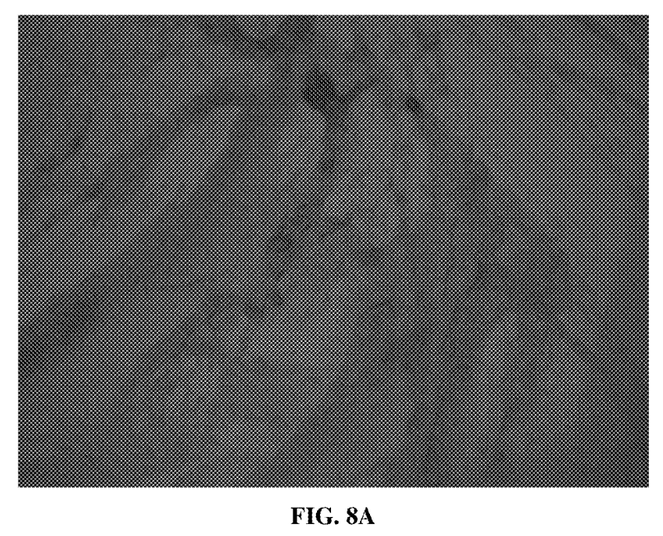
FIG. 8A is an excitation light image of a sample obtained by a portion of excitation light according to an embodiment of the presently claimed invention.
Figure 8B:
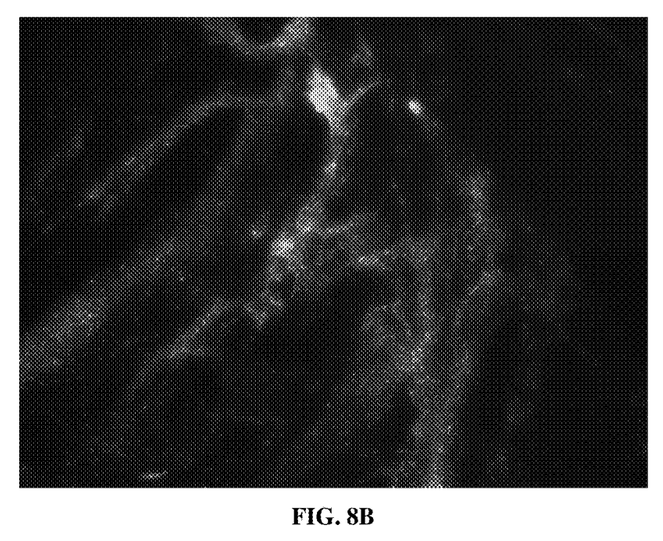
FIG. 8B is a fluorescence image of the sample obtained by fluorescence light.

FIG. 8A is an excitation light image of a sample obtained by a portion of excitation light according to an embodiment of the presently claimed invention. FIG. 8B is an images of the sample obtained by fluorescence light. Although the exposure time for the excitation light image of FIG. 8A is shorter than that of FIG. 8B, FIG. 8A is lighter than FIG. 8B, implying that more light has been received for imaging by using the portion of excitation light.

According to one embodiment of the presently claimed invention, when laser or LED is used as the excitation light source, an excitation filter may not be required since the LED is able to provide a specific band of wavelengths.

According to one embodiment of the presently claimed invention, a ratio of transmission to reflection performed by the beam splitter in the focusing module is 80 to 20.

According to one embodiment of the presently claimed invention, excitation filters can be placed as a separated filter changing device (e.g. filter wheel or slider) away from the filter turret. And such separated filter changing device can be placed between the excitation light source and the focusing module.

The embodiments disclosed herein may be implemented using a general purpose or specialized computing device, computer processor, or electronic circuitry including but not limited to a digital signal processor (DSP), application specific integrated circuit (ASIC), a field programmable gate array (FPGA), and other programmable logic device configured or programmed according to the teachings of the present disclosure. Computer instructions or software codes running in the general purpose or specialized computing device, computer processor, or programmable logic device can readily be prepared by practitioners skilled in the software or electronic art based on the teachings of the present disclosure.

In some embodiments, the present invention includes a computer storage medium having computer instructions or software codes stored therein which can be used to program a computer or microprocessor to perform any of the processes of the present invention. The storage medium can include, but is not limited to, floppy disks, optical discs, Blu-ray Disc, DVD, CD-ROMs, and magneto-optical disks, ROMs, RAMs, flash memory devices, or any type of media or device suitable for storing instructions, codes, and/or data.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

What is claimed is:

1. A focusing apparatus for a fluorescence microscope, comprising:
    an excitation light source for emitting excitation light used to excite a sample;
    a first beam splitter for reflecting the excitation light towards the sample via an objective lens, and transmitting fluorescence light emitted from the sample; and
    a focusing module located between the excitation light source and the first beam splitter, wherein the focusing module comprises a reflecting optical device used for light reflection and a focus imaging camera, wherein the reflecting optical device is located in a pathway of the excitation light between the excitation light source and the first beam splitter;

wherein the sample reflects, backward scatters, or reflects and backward scatters a first portion of the excitation light towards the first beam splitter, and the first beam splitter reflects the first portion of the excitation light towards the reflecting optical device, and the reflecting optical device reflects a second portion of the excitation light towards the focus imaging camera; and wherein the second portion of the excitation light captured by the focus imaging camera forms at least one excitation light image of the sample for focusing of fluorescence imaging.

2. The focusing apparatus of claim 1, wherein the reflecting optical device is a second beam splitter, and the second portion of the excitation light is a portion of the first portion of the excitation light.

3. The focusing apparatus of claim 1, wherein the reflecting optical device is a mirror, and the second portion of the excitation light is same as the first portion of the excitation light.

4. The focusing apparatus of claim 1, further comprising:
a collector lens located between the first beam splitter and the reflecting optical device.

5. The focusing apparatus of claim 1, further comprising:
a collector lens located between the excitation light source and the reflecting optical device.

6. The focusing apparatus of claim 5, wherein the focusing module further comprises a tube lens located between the reflecting optical device and the focus imaging camera.

7. The focusing apparatus of claim 1, further comprising:
an excitation filter located between the excitation light source and the first beam splitter.

8. The focusing apparatus of claim 7, further comprising:
more than one excitation filter and more than one first beam splitter to form more than one filter combination optical block to perform multiplex focusing.

9. The focusing apparatus of claim 1, further comprising:
a central processing unit for determining a focus plane of a fluorescence image based on the excitation light image.

10. A focusing apparatus for a fluorescence microscope, comprising:
an excitation light source for emitting excitation light used to excite a sample;
a beam splitter for reflecting the excitation light towards the sample via a first objective lens, and transmitting fluorescence light emitted from the sample; and
a focusing module located beneath the sample, wherein the focusing module comprises a converging lens used for converging light, and a focus imaging camera, wherein the converging lens is located between the sample and the focus imaging camera;
wherein a portion of the excitation light transmits through the sample, and the portion of the excitation light travels towards the converging lens, and is converged by the converging lens towards the focus imaging camera; and
wherein the portion of the excitation light captured by the focus imaging camera forms at least one excitation light image of the sample for focusing of fluorescence imaging.

11. The focusing apparatus of claim 10, wherein the converging lens is a second objective lens.

12. The focusing apparatus of claim 10, further comprising:
an excitation filter located between the excitation light source and the beam splitter.

13. The focusing apparatus of claim 12, further comprising:
more than one excitation filter and more than one beam splitter to form more than one filter combination optical block to perform multiplex focusing.

14. The focusing apparatus of claim 10, further comprising:
a central processing unit for determining a focus plane of a fluorescence image based on the excitation light image.

15. A focusing method for a fluorescence microscope, comprising:
emitting excitation light for illuminating a sample via an objective lens, wherein the excitation light is reflected towards the sample by a first beam splitter;
performing one of:
reflecting, backward scattering, or reflecting and backward scattering a first portion of the excitation light by the sample towards the first beam splitter, reflecting the first portion of the excitation light by the first beam splitter towards a reflecting optical device, and reflecting a second portion of the excitation light by the reflecting optical device towards a focus imaging camera; and
transmitting a third portion of the excitation light through the sample, and converging the third portion of the excitation light towards a focus imaging camera; and
forming at least one excitation light image with the second portion of the excitation light, or the third portion of the excitation light by the focus imaging camera for focusing of fluorescence imaging.

16. The focusing method of claim 15, further comprising:
changing a distance between the objective lens and the sample, and repeating the above steps until a focus plane of the sample for the fluorescence imaging is determined.

17. The focusing method of claim 15, further comprising:
transmitting fluorescence light emitted from the sample towards a fluorescence imaging camera via the first beam splitter for forming at least one fluorescence image.

18. The focusing method of claim 15, further comprising:
taking at least one fluorescence image with fluorescence light emitted from the sample by a fluorescence imaging camera simultaneously with the step of forming the excitation light image to perform predictive focusing, wherein a field of view of the fluorescence image is different from a field of view of the excitation light image.

19. The focusing method of claim 15, wherein the reflecting optical device is a second beam splitter, and the second portion of the excitation light is a portion of the first portion of the excitation light.

20. The focusing method of claim 15, wherein the reflecting optical device is a mirror, and the second portion of the excitation light is same as the first portion of the excitation light.

* * * * *